United States Patent
Smith et al.

(10) Patent No.: US 6,402,724 B1
(45) Date of Patent: Jun. 11, 2002

(54) WOUND IRRIGATION SHIELD

(75) Inventors: Steven M. Smith; Mark A. Christensen, both of Salt Lake City, UT (US); Deborah K. Jacobson, Saukville, WI (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 0 days.

(21) Appl. No.: 09/260,626

(22) Filed: Mar. 1, 1999

Related U.S. Application Data

(63) Continuation-in-part of application No. 08/925,866, filed on Sep. 2, 1997, now Pat. No. 6,293,929.

(51) Int. Cl.$^7$ .............................................. A61M 35/00
(52) U.S. Cl. ...................................... 604/289; 604/268
(58) Field of Search ................................ 604/187, 317, 604/289, 304, 305, 308, 310, 540, 543, 36, 37, 38, 39, 40, 192, 263, 268, 275–279, 290, 311, 355; 239/103, 104, 110; 606/123; 433/116; D24/107, 108, 112, 111, 119, 120

(56) References Cited

U.S. PATENT DOCUMENTS

| | | | |
|---|---|---|---|
| 2,898,911 A | * | 8/1959 | Taylor |
| 3,026,874 A | * | 3/1962 | Stevens ........................ 128/260 |
| 3,288,140 A | | 11/1966 | McCarthy |
| 3,648,696 A | * | 3/1972 | Keith .......................... 128/248 |
| 3,887,115 A | * | 6/1975 | Petterson ................ 222/402.13 |
| 4,376,437 A | | 3/1983 | Sundheim et al. |
| 4,692,140 A | * | 9/1987 | Olson |
| 4,769,003 A | | 9/1988 | Stamler |
| 4,807,625 A | * | 2/1989 | Singleton ..................... 128/361 |
| 4,898,588 A | | 2/1990 | Roberts |
| 5,224,940 A | | 7/1993 | Dann et al. |
| 5,241,969 A | | 9/1993 | Carson et al. |
| 5,248,307 A | | 9/1993 | Sokoloff |
| D344,133 S | | 2/1994 | Stamler |
| D345,016 S | * | 3/1994 | Stamler |
| 5,376,003 A | | 12/1994 | Rizkalla |
| 5,441,174 A | | 8/1995 | Sperry |
| 5,480,410 A | | 1/1996 | Cuschieri et al. |
| 5,496,290 A | | 3/1996 | Ackerman |
| 5,554,132 A | | 9/1996 | Straits et al. |
| 5,624,419 A | | 4/1997 | Ersek et al. |
| 5,833,675 A | * | 11/1998 | Garcia ......................... 604/310 |
| 5,913,832 A | * | 6/1999 | Sagalovich et al. |
| 5,941,859 A | * | 8/1999 | Lerman ....................... 604/289 |
| 6,050,981 A | * | 4/2000 | Lampropoulos et al. |
| 6,156,004 A | * | 12/2000 | Tremaine et al. |

FOREIGN PATENT DOCUMENTS

WO      WO 97/48427      12/1997

OTHER PUBLICATIONS

Hellewell et al, "A Cytotoxicity Evaluation of Antimicrobial and Non–Antimicrobial Wound Cleansers" from *Wounds: A Compendium of Clinical Research and Practice* vol. 9, No. 1, pp. 15–19.

Advertisement: Baxter Health Care Corp., "With Squirt Cap: Irrigation cap with syringe tip".

US Department of Health and Human Services, "Treatment of Pressure Ulcers" from *Clinical Practice Guideline* No. 15, pp. 18–19, 50–52, 63–65.

* cited by examiner

*Primary Examiner*—Sharon Kennedy
*Assistant Examiner*—Catherine Serke
(74) *Attorney, Agent, or Firm*—TraskBritt

(57) ABSTRACT

A splash shield for use in wound irrigation comprises a three-dimensional shield member having a peripheral edge and a surface extending from the peripheral edge, the shield member being formed at least in part of flexible and pliant material for selectively shaping the peripheral edge to fit the shape or dimension of a wound, and an adjustable hub extending from the surface of the shield member configured to be circumferentially adjustable to adapt to the fluid end portion of any number and variety of irrigation fluid delivery devices. An attachable drain tube and a splash shield having an attached drain tube for removing fluid from the wound site is also disclosed.

15 Claims, 2 Drawing Sheets

WOUND IRRIGATION SHIELD

CROSS-REFERENCE TO RELATED APPLICATION

This application is a continuation-in-part of Ser. No. 08/925,866, filed Sep. 2, 1997 now U.S. Pat. No. 6,293,929.

BACKGROUND

1. Field of the Invention

This invention relates to medical devices used in irrigating and cleansing wound sites on patients, and is specifically related to splash shields for preventing the back splash of fluids from a wound during wound irrigation so that the wound fluids do not contact the attending medical caregiver.

2. Statement of the Art

It is well-known that wounds to the body which occur through injury or accident, through surgical procedure, or which are caused by compromised circulation, such as pressure ulcers, must often be cleansed to keep the wound free of bacteria and other deleterious matter which may compromise the rate at which the wound heals. Cleansing of the wound often involves irrigating the wound with a stream or spray of liquid, such as isotonic saline or other sterile solution. Current clinical practice guidelines indicate that an irrigation pressure of between four to fifteen pounds per spare inch is effective for the cleansing of pressure ulcers or other chronic wounds. That amount of pressure is sufficient for removal of foreign particles, debris and bacteria to thereby promote healing and minimization of infection or inflammation, yet low enough to avoid or minimize damage to regenerating granulation tissue in the wound. The guidelines also recommend the use of high pressure irrigation for mechanical debridement to remove the devitalized tissue.

Delivery of the irrigating liquid to the wound site is usually accomplished by pumping liquid from a hypodermic syringe through an attached needle, or catheter, trained toward the wound site. Most of the liquid delivered to a wound site flows away from the wound site and is usually collected in some manner, such as in a bowl or with absorbent material. However, some back splash of fluid and debris from the wound occurs, especially at higher pressures of liquid delivery. The liquid back splash contains not only irrigating liquid, but fluid from the wound and loose matter extracted from the wound—particularly in situations where wound irrigation is conducted for debridement of the wound. It is unpleasant and potentially dangerous to have the back splash liquid from the wound strike the medical personnel conducting the irrigation procedure or the patient, or to have the material contaminate the environment. Current OSHA guidelines regarding blood-borne pathogens require the minimization of the splatter and splashing of blood and the creation or aerosols containing potentially contaminated body fluids. Therefore, shield devices have been developed in the art to protect the caregiver from being exposed to the back splash.

Examples of wound irrigating back splash shields are disclosed in U.S. Pat. No. 4,692,140 to Olson, U.S. Pat. No. 4,669,003 to Stamler, U.S. Pat. No. 4,989,588 to Roberts, U.S. Pat. No. 5,224,940 to Dann, et al., U.S. Pat. Des. No. 344,133 to Stamler, U.S. Pat. Des. No. 345,016 to Stamler, U.S. Pat. No. 5,376,003 to Rizkalla, U.S. Pat. No. 5,441,174 to Sperry and U.S. Pat. No. 5,496,290 to Ackerman. Most of the shields disclosed in the referenced patents are rigid and are, therefore, unadaptable to the variation in wound shapes which occur. As a result, back splash liquid can still escape the confines of such shields. More importantly, rigid prior art shields can damage the regenerating tissue of a wound if the rigid circumferential edge of the shield is pressed against, scraped along, or otherwise contacted with the wound.

Most of the shields disclosed in the referenced patents are configured with a liquid delivery conduit which is positioned in alignment with a central longitudinal axis of the shield so that liquid delivery is strictly along that central longitudinal axis. The configuration of such devices requires the fluid delivery apparatus (i.e., typically a hypodermic syringe) to be positioned in vertical alignment with the wound to effectuate liquid delivery. The location of a wound on a patient is not always so accommodating. For example, a wound on the back of a patient who cannot be moved or rotated significantly from a supine position requires the caregiver to position himself and the irrigation device at a difficult angle to reach the wound. Furthermore, even those shields which are configured to provide a fluid conduit which is not strictly oriented along a longitudinal axis of the shield are unable to be angularly adjusted to modify the direction of liquid delivery to the wound.

Clinical practice guidelines requiring an irrigation pressure of 4 to 15 psi for the effective cleaning of wounds also impose an additional requirement for wound irrigating devices which is not addressed in prior art devices. It is left to the judgment of the caregiver to determine when and if the irrigating fluid is being delivered to the wound within the required range or pressure. The failure to irrigate the wound at the appropriate fluid pressure can adversely affect the health and healing of the wound, and ultimately the patient. The importance of proper irrigation is further complicated by the fact that some patients, such as elderly or frail patients, often have wounds that do not heal, or the tissue does not regenerate rapidly. Thus, fluid delivered at too high a pressure may compromise the healing process, and fluid deliberately delivered at a lower pressure may be inadequate for cleaning the wound.

Using conventionally known wound irrigating devices, the caregiver must depress with the thumb and fingers the plunger of a 35 cc hypodermic syringe filled with irrigating fluid and fitted with a 19 gauge needle of one and one half inches in length to produce an 8 psi delivery of irrigating fluid. That methodology assumes that all caregivers have the same degree of manual strength to depress the plunger and does not take into consideration that the caregiver's hand tires after repeated fillings and evacuations of the syringe in a single wound irrigating episode, thereby leading to less and less pressure being applied to depression of the plunger. Another factor leading to uneven or inconsistent fluid pressure at delivery is the mechanics of hand movement leading to different pressure being applied to the plunger when the plunger is fully extended from the syringe barrel (and the thumb is displaced farther from the fingers) as opposed to when the plunger is almost fully positioned in the barrel (and the thumb is closer to the fingers). The difficulty of providing a sufficient and steady delivery of fluid to the wound site has been addressed in part by the development of different fluid delivery devices, such as spray bottles, squirt bottles, aerosol cannisters or water wands. While such devices have addressed the issue of fluid delivery to a wound site, such devices have not addressed the problem of back splash.

Thus, it would be beneficial to the art to provide a wound irrigation splash shield which is universally adaptable to all types of fluid delivery devices that are used in wound irrigation procedures, which is adaptable to the differences in wound dimension and body contour, and which provides a degree of angular adjustability to facilitate delivery of the irrigating fluid to a wound site while still providing protection from the back splash of fluid and other debris from the wound.

SUMMARY OF THE INVENTION

In accordance with the present invention, a wound irrigation splash shield is provided which is universally adaptable to fit a variety of known fluid delivery devices designed for delivering fluid to a wound site. The splash shield of the present invention comprises a three-dimensional shield configured to provide protection from back splash during wound irrigation procedures and has an adjustable fluid entry hub which is conformable or adaptable to a variety of fluid delivery devices used for delivering an irrigation fluid to a wound site. The splash shield is structured to be at least partially flexible to provide selective angular positioning of the hub, and thus a fluid delivery device attached to the hub, to selectively direct fluid to the wound site.

The shield of the present invention may generally be hemispherical in shape, has a peripheral edge which is positionable near or against the patient's body and has a substantially continuous dome-like surface extending upwardly from the peripheral edge. The peripheral edge, in lateral cross section, may be circular, oval, oblong or any other suitable shape. The shield member is formed at least partially of a flexible or compliant material which renders the shield member conformable to any shape or dimension of a wound and renders it conformable to the topography of the body. In those embodiments where the shield member is only partially made of a flexible material, the flexible or compliant portion is located near the peripheral edge of the shield member and the less flexible, or comparatively rigid, portion of the shield member is located away from the peripheral edge. Thus, the peripheral edge, in any embodiment of the invention, is flexible so that it can be manipulated to be formed about the unique shape or dimension of the wound and the body's contour and, more importantly, so that if the shield should come in contact with the wound, it will flex and not damage the tender tissues of the wound.

The shield may be structured in any suitable manner to be flexible at the peripheral edge, but substantially inflexible or comparatively rigid in other regions of the shield. The shield may then, for example, be formed by varying the thickness of the material from near the apex of the shield to the peripheral edge, by fabricating the shield from materials having a different modulus of elasticity, by removing plasticizers from the material of the shield in the area where increased stiffness or rigidity is desired, by adding plasticizers in areas where flexibility is desired or by using reinforcing longitudinal ribs incorporated into the material or structure of the shield.

The peripheral edge of the shield member may be planar (i.e., every point along the entire peripheral edge contacts a planar surface) to contain more back splash liquid in the shield, or the peripheral edge may be non-linear, such as being scalloped, to allow fluid to exit between the peripheral edge of the shield member and the patient's skin. Additionally, at least one aperture may be formed through the surface of the shield member to allow fluid displacement or release of fluid from the shield. In accordance with one aspect of the invention disclosed herein, the shield may be structured with a peripheral edge which is planar, thereby rendering the peripheral edge capable of encircling the wound site and preventing fluid from escaping between the patient's skin and the peripheral edge, and is further structured with a drain tube formed in the shield member near the peripheral edge and extending away from the shield member to direct irrigation fluid and fluids or debris from the wound site away from the shield member. The drain tube may be any suitable length and may be configured to extend to a receptacle for collecting the drained fluid or may be configured for attachment to a conventional medical suction device. As also disclosed herein, the drain tube may be attachable to the shield by an adapter collar or the like.

The shield of the invention may, in one embodiment, be wholly flexible throughout the structure, thereby providing the greatest degree of manipulation of the shield to fit the shape or dimension of the wound and the contour of the body. The shield of the invention, in another embodiment, may be partially flexible and partially inflexible or comparatively rigid. In either embodiment, the shield is structured with a circumferentially-adjustable hub configured to receive the end portion of any variety of fluid delivery devices. By "circumferentially-adjustable," it is meant that at least the internal diameter of the hub may be modified in some fashion to accommodate the unique diameter of the fluid-dispensing end portion or tip of any irrigation fluid delivery device. Fluid devices that may be received by the adjustable hub include any conventional device specifically designed for delivering an irrigation fluid to a wound site and any fluid delivery device that may be suitably adaptable to the purpose of delivering an irrigation fluid to a wound site. Conventional irrigation fluid delivery devices include, but are not limited to, spray bottles (e.g., Sea-Clens™ manufactured by Sween Corp., Mankato, Minn.), water wands (e.g., The Water Pik-™ manufactured by Teledyne, Fort Collins, Colo.), squeeze bottles (e.g., the Squirt Cap™ manufactured by Baxter, Chicago, Ill.), syringes, aerosol cannister, atomizers and water pistols.

The circumferentially-adjustable hub may be configured in any manner which will enable the hub to attach to and secure the fluid-dispensing end portion, or other suitable portion, of a fluid delivery device of any given type or construction. For example, the adjustable hub may be formed as a flexible throat extending outwardly from the surface of the shield, the flexible throat being sufficiently elastic to expand to the diameter and geometry of the fluid-dispensing end portion of the fluid delivery device to thereby engage it. In an alternative embodiment, the adjustable hub may be configured as a flexible collar having an inner circumferential surface which is adjustable to expand or enlarge to engage the end portion of a fluid delivery device. In yet another alternative embodiment, the adjustable hub may be formed with an eccentric, rotatable cuff which secures the hub to the fluid-dispensing end portion of a fluid delivery device. The adjustable hub is preferably configured with an opening which is expandable enough to secure the end portion of a fluid delivery device, but which is also structured to prevent the end portion or tip of any such fluid delivery device from extending too far into the interior of the shield, thereby preventing the tip or end of the fluid delivery device from coming in contact with the wound site.

The adjustable hub of the shield member may be located at the center or apex of the shield member. Alternatively, the adjustable hub may be located away from the center or apex of the shield so that the fluid is delivered to the wound site at an angle to a longitudinal axis oriented perpendicularly to the plane of the peripheral edge of the shield member. Regardless of the placement or positioning of the adjustable hub relative to the body of the shield, the area of the shield member immediately surrounding the adjustable hub is structured to allow the hub to be angularly repositioned relative to the shield member so that the angle of the liquid moving through the adjustable hub may be selectively modified. By so configuring the shield member, the angle at which irrigating liquid is delivered to the wound site may be selected in accordance with the unique requirements of the wound (e.g., shape, depth, dimension, sensitivity). That is, some wounds are shallow and the tissues are delicate so that delivery of liquid in a directly vertical orientation to the wound, particularly at higher pressures, may cause tearing of the delicate tissues. Delivering liquid at an angle to the wound is less traumatic to the tissues, even at elevated pressure levels, and modifying the direction or angle of the spray insures that the entire area of the wound can be bathed with irrigation fluid at a desired pressure. It may be particularly suitable to form the shield member with angle indicia near the adjustable hub to direct the user in appropriately modifying the angle of the spray.

The features of the shield of the present invention are more fully understandable when considered in connection with the following description of the illustrated invention.

BRIEF DESCRIPTION OF THE ILLUSTRATIONS

In the drawings, which illustrate what is currently considered to be the best mode for carrying out the present invention:

DETAILED DESCRIPTION OF THE ILLUSTRATIONS

Figure 1:
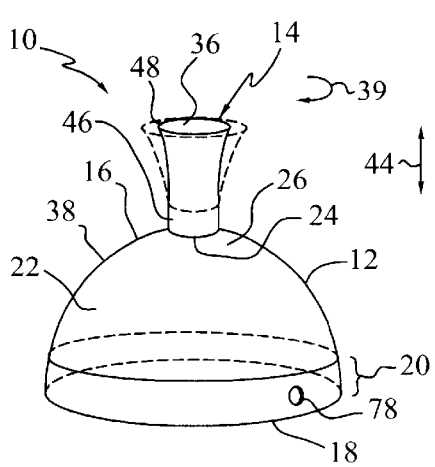
FIG. 1 is a perspective view of a first embodiment of the shield of the present invention.

A first embodiment of the splash shield 10 of the present invention is illustrated in FIG. 1. The shield 10 is generally comprised of a three-dimensional shield member 12 and an adjustable hub 14 extending outwardly from an exterior surface 16 of the shield member 12. The three-dimensional shield member 12 of the present invention is generally hemispherical in shape, as shown, but may take any suitable form, size, shape, dimension or design which prevents back splash of irrigating fluid and wound fluid or debris. In principal, the shield member 12 may be structured as a wholly flexible form, or the shield member 12 may be partially flexible and partially inflexible or comparatively rigid. Regardless of whether the shield member 12 is a wholly- or partially-flexible embodiment, the shield member 12 is formed to be flexible at the peripheral edge 18 of the shield member 12. Flexibility enables manipulation of the peripheral edge 18 to fit the unique shape or dimension of a wound and the contour of the patient's body and, more importantly, prevents damage to the sensitive wound area if the peripheral edge 18 should come in contact with the wound. It is also a principal element of the present invention that the shield member 12 be formed so that the immediate area about where the hub 14 is positioned is flexible so that the angle or orientation of the hub 14, and thus the fluid delivery device attached to the hub 14, may be selectively modified relative to the wound and to the shield member 12.

Figure 3:
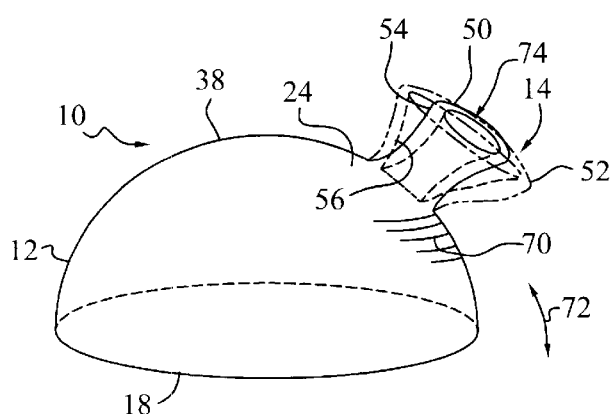
FIG. 3 is a perspective view of a second embodiment of the shield of the present invention.

In the embodiment of the invention shown in FIG. 1, the shield member 12 is formed with a width 20 of flexible material extending a distance from the peripheral edge 18. The portion 22 of the shield member 12 extending from the flexible width 20 to near the apex 24 of the shield member 12 may be substantially inflexible or comparatively rigid, except for the area 26 immediately around the hub 14, which remains relatively compliant to allow the angle of the hub 14 to be modified relative to the wound site (which would be located beneath the shield member 12). By contrast, the shield member 12 shown in FIG. 3 is structured as a homogeneously flexible or compliant body (i.e., equally flexible at all points about the shield member 12).

Figure 5:
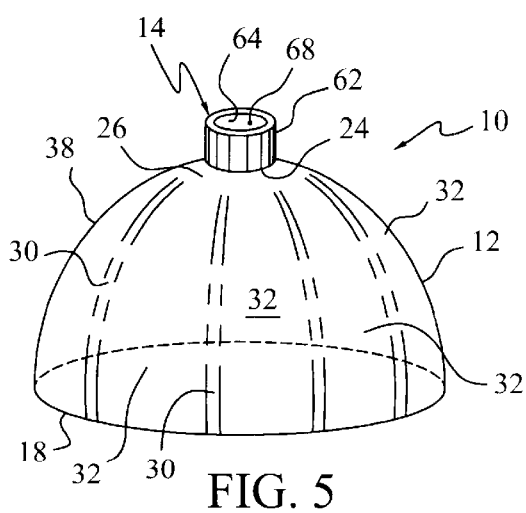
FIG. 5 is a perspective view of a third embodiment of the shield of the invention.

In still another alternative embodiment of the shield member 12 shown in FIG. 5, the shield member 12 is structured with some longitudinal rigidity by virtue of the incorporation into the shield member 12 of longitudinal stiffening ribs 30. The longitudinal rib members 30 extend from near the hub 14 to near the peripheral edge 18. The rib members 30 may be made of substantially rigid, or only slightly flexible, plastic strips which are incorporated into the flexible plastic material of the shield member 12, or the rib members 30 may be formed by treating longitudinal sections 32 of the shield member 12, originally formed of hardened plastic material, with plasticizers to render sections 32 of the shield member 12 flexible. Alternatively, the rib members 30 may be formed by increasing the thickness of longitudinal sections of the shield member 12, Again, the area 26 about the adjustable hub 14 remains flexible to allow the hub 14 to be selectively angled relative to the wound site as previously described.

The circumferentially-adjustable hub 14 of the present invention may take any form which enables the hub 14 to be modified to accommodate the fluid-dispensing end portion or tip of any fluid delivery device. More specifically, the hub 14 is structured with an internal circumferential surface the size or shape of which is modifiable to accommodate the fluid end portion of a variety of fluid delivery devices. The external aspects of the hub 14 may be circumferentially modifiable as well. Some examples of suitable embodiments for carrying out the invention are described below, but are not intended to limit the possible configurations of an adjustable hub suitable for use in the invention.

Figure 2:
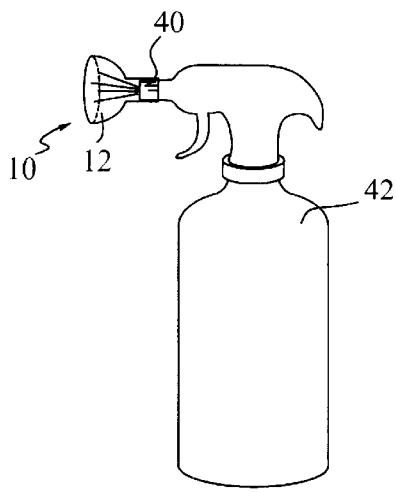
FIG. 2 is a perspective view of the shield of FIG. 1 attached to a spray bottle, as but one example of an irrigation fluid delivery device.

A first exemplar embodiment of the adjustable hub 14 is shown in FIG. 1 where the hub 14 is structured as a flexible throat 36 extending from the surface 38 of the shield member 12. The flexible throat 36 is elastic at least in a circumferential direction, suggested by arrow 39, to allow the diameter of the throat 36 to expand outwardly and inwardly, as suggested by the dotted lines. Thus, the flexible throat 36 is capable of being increased in diameter to encircle the fluid end portion of a fluid delivery device. This principal is illustrated in FIG. 2 where the adjustable hub 14 of the invention shown in FIG. 1 is increased in diameter to fit about, or encircle, the fluid-dispensing tip 40 of a spray bottle 42. Because of the elasticity of the adjustable hub 14, the shield member 12 is held firmly in place relative to the spray bottle 42 and will not slip off. In a similar manner, the flexible throat 36 of the illustrated embodiment may be increased in diameter to fit virtually any size, geometry (i.e., circular or square) or dimension of a fluid-dispensing end portion or tip of any fluid delivery device.

The flexible throat 36 shown in FIG. 1 may also be elastic in a longitudinal direction, suggested by arrow 44, to further enable a competent engagement with the fluid end portion or tip of a fluid delivery device, but such longitudinal elasticity is not required. Further, as shown in FIG. 1, the flexible throat 36 may optionally be structured with a stabilizing band 46 positioned near the surface 38 of the shield member 12 to help maintain the longitudinal stability of the flexible throat 36. The stabilizing band 46 may be structured by decreasing the plasticity of the flexible throat 36 in that region or by molding the shield member 12 with a stiffening device. It is preferred, however, that the stabilizing band 46 itself maintain circumferential elasticity to accommodate the receipt of the shield member 12 on the fluid end portion of a fluid delivery device. Further, the stabilizing band 46 does not modify the fact that the hub 14 is angularly movable relative to the shield member 12 in the area 26 surrounding the hub 14.

In attaching the adjustable hub 14 to the fluid end portion or tip of a fluid delivery device, the outer lip 48 of the flexible throat 36 may be everted, or folded back, over the flexible throat 36 toward the surface 38 of the shield member 12. The fluid end portion or tip of a fluid delivery device may then be inserted into the hub 14 followed by rolling the outer lip 48 of the flexible throat 36 back up to extend the flexible throat 36 its full length and to encircle the fluid end portion of the fluid delivery device.

Figure 4:
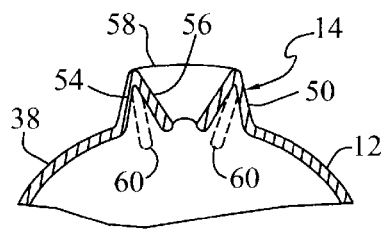
FIG. 4 is a view in cross section of the embodiment shown in FIG. 3.

FIGS. 3 and 4 show a second exemplar embodiment of the circumferentially adjustable hub 14 where the hub 14 is structured as a flexible collar 50. In one embodiment, the flexible collar 50 may be capable of being circumferentially increased, as suggested by the dotted lines 52 in FIG. 3. Alternatively, however, the outer portion 54 of the flexible collar 50 may be relatively inelastic. As illustrated more specifically in FIG. 4, the flexible collar 50 is configured with an outer portion 54 which extends outward from the surface 38 of the shield member 12 and an inner portion 56 which is an inward invagination of the outer portion 54. The inner portion 56 is essentially pivotable relative to the outer portion 54 by virtue of the connection between the inner portion 56 and the outer portion 54 at the upper rim 58 of the flexible collar 50. Thus, the inner portion 56, which is circumferentially elastic as suggested by the dotted lines 60, is capable of expanding circumferentially to accommodate the insertion of the fluid end portion or tip of a fluid delivery device (e.g., the tip of a Water Pik™) to hold it in place within the shield member 12 for fluid delivery to a wound site. Again, as suggested in FIG. 3, the flexible collar 50 may be structured so that both the outer portion 54 and the inner portion 56 are circumferentially elastic to increase in diameter, thereby enabling the shield member 12 to be attached to the fluid end of any variety of fluid delivery devices.

Figure 6:
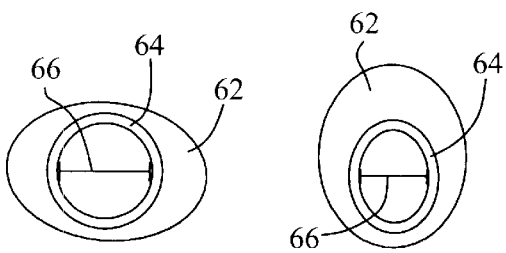
FIG. 6 is a plan view of the adjustable hub of the embodiment shown in FIG. 5 when the rotatable cuff is in an open position.
Figure 7:
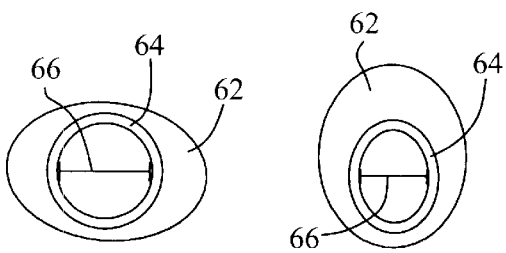
FIG. 7 is a plan view of the adjustable hub of the embodiment shown in FIG. 5 when the rotatable cuff is in a closed or engaging position.

In a third exemplar embodiment of the circumferentially-adjustable hub 14 shown in FIG. 5, an eccentric, rotatable cuff 62 encircles an inner threaded band 64 which extends outward from the surface 38 of the shield member 12. The inner threaded band 64 is substantially less flexible than the shield member 12 to enable the inner band to have longitudinal stability, but is still moderately circumferentially flexible. Notably, the area 26 about the hub 14 may still be rendered flexible to enable the hub 14 to be selectively angled relative to the wound site. As shown in FIGS. 6 and 7, the cuff 62 is configured to be non-circular and eccentrically rotatable relative to the inner band 64. Thus, as shown in the illustrations, the cuff 62 is ovate and encircles the inner band 64, which is substantially circular. When the cuff 62 is rotated to what may be considered the open position, illustrated in FIG. 6, the inner band 64 maintains a substantially circular diameter 66. However, because the cuff 62 is eccentrically pivoted relative to the inner band 64, when the cuff 62 is rotated to what may be considered the closed or engaging position, illustrated in FIG. 7, the ovate configuration of the cuff 62 deforms the inner band 64 thereby decreasing or modifying the dimension of the inner diameter 66 of the inner band 64 to cause the inner band 64 to grip the fluid end portion of a fluid delivery device positioned in the opening 68 of the hub 14. Conversely, when the cuff 62 is rotated in the opposite direction, the deformation of the inner band 62 is relieved and the inner band 64 ceases to engage the fluid end portion of the fluid delivery device.

It is notable that the hub 14 of the present invention may be located at any desirable position relative to the shield member 12. That is, as shown in FIG. 1, the hub 14 may be positioned at the apex 24 of the shield member 10 so that the hub 14 is axially aligned along the longitudinal axis of the shield member 10. Alternatively, as shown in FIG. 3, the adjustable hub 14 may be positioned away from the apex of the shield member 12, thereby naturally positioning the fluid delivery device (not shown) connected to the hub 14 at an appropriate angle to the wound. By selectively positioning the hub 14 at an angle to the wound site, damage to the tender tissues of the wound can be avoided, and directing the back splash at a given angle to the wound can be more easily controlled. Regardless of the location of the hub 14 relative to the shield member 12, the area 26 surrounding the hub 14 is preferably flexible to further allow the hub 14 to be angularly positioned relative to the wound site.

Because the adjustable hub 14 of the present invention may, most suitably, be angularly adjustable relative to the wound site to selectively modify the angle at which fluid is delivered to the wound site, the splash shield 10 of the present invention may be configured with indicia 70, as shown in FIG. 3, which are borne on the outer surface 38 of the shield member 12 in proximity to the hub 14. The indicia 70 assist the user in determining a desired change in the angle of spray of the irrigating liquid as the angle of the hub 14 is modified in the direction of arrow 72. The hub 14 may also bear an appropriate marking 74 which assists in aligning the hub 14 with the indicia 70 to achieve a desired angle of spray or fluid flow. The indicia 70 may be marked, for example, in degrees of angularity (e.g., 90°, 60°, 45°) relative to the longitudinal axis of the shield member 12. The indicia 70 may also, for example, be marked with increments of length (e.g., −6 mm, −4 mm, −2 mm, 0, 2 mm, 4 mm, 6 mm) to indicate the distance from the longitudinal axis the spray is being directed. Any other suitable form or type of indicia may be employed.

As shown in FIG. 1, the shield member 12 of the present invention may also be configured with at least one aperture 78 for providing means for releasing fluid from beneath the shield member 12 during or after an irrigation procedure. The aperture or apertures 78 may preferably be located near the peripheral edge 18 of the shield member 12, but may be located anywhere through the shield member 12.

Figure 8:
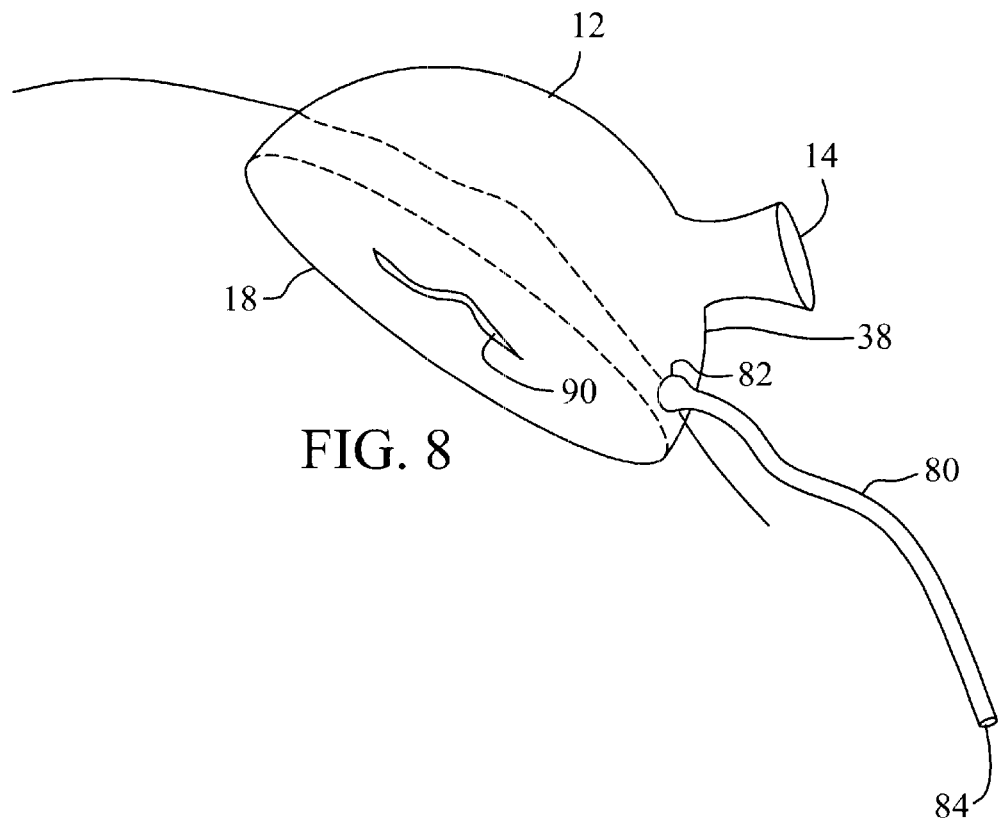
FIG. 8 is a perspective view of an alternative embodiment of the invention configured with a drain tube.
Figure 9:
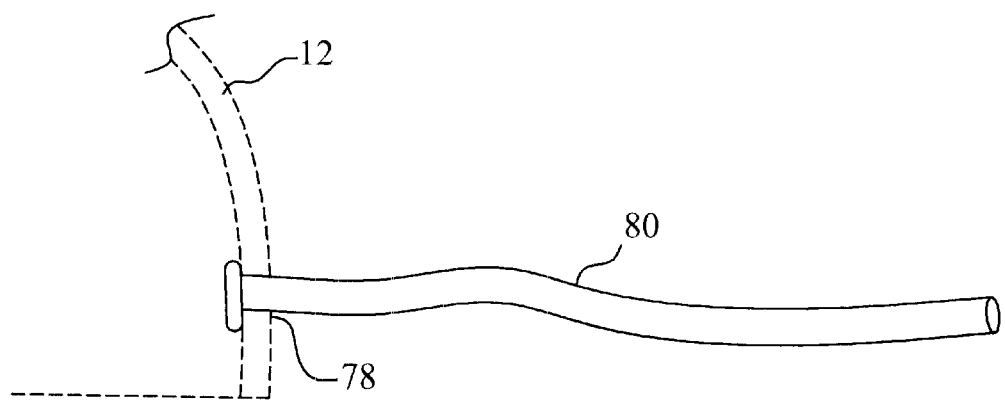
FIG. 9 is a perspective view of a drain tube having an adapter collar for adapting the drain tube to a shield member.

As shown in FIG. 8, the shield member 12 may be configured with a drain tube 80 having a first end 82 formed to the outer surface 38 of the shield member 12 and a second end 84 distanced from the shield member 12 to deliver irrigating fluid from beneath the shield member 12 and environment of the wound site 90. The first end 82 of the drain tube 80 is preferably located near the peripheral edge 18 of the shield member 12 to facilitate the draining of fluid from the wound site 90. The length of the drain tube 80 may vary, but may be particularly sized in length to extend the second end 84 of the drain tube to a receptacle into which fluid moving through the drain tube 80 can be collected for disposal. The second end 84 of the drain tube may be adapted to attach to a suction device of the type which is conventionally available in medical or hospital settings to aspirate fluid from beneath the shield member 12. The drain tube 80 disclosed herein may be suitably used with a shield member 12 as described herein or with any other splash shield design previously disclosed in any prior application hereto. To that end, as shown in FIG. 9, a separate drain tube 94 having an adapter connection 96 at the first end 82 may be provided for attaching the drain tube 80 to an existing shield member 12 which is structured with an aperture 78, such as is shown in FIG. 1. The adapter connection 96 may be integrally formed with the drain tube 80 as shown in FIG. 9 or may be separate and attachable to both the shield member 12 and the drain tube 80.

The splash shield of the present invention is particularly configured to enable the shield to be adapted to a variety of fluid delivery devices which have been specifically designed for delivering irrigation fluid to a wound site, and to enable the shield to be adapted to other fluid delivery devices that may not have been specifically designed for irrigating wound sites, but which nonetheless are suitable to that purpose. The adjustable hub of the splash shield may be configured, therefore, in any suitable manner which allows the splash shield to be conjoined with a fluid delivery device. Thus, reference herein to specific details of the illustrated embodiments is by way of example and not by way of limitation. It will be apparent to those skilled in the art that many modifications of the basic illustrated embodiment may be made without departing from the spirit and scope of the invention as recited by the claims.

What is claimed is:

1. A splash shield for use in wound irrigation comprising:
    a three-dimensional shield member having a peripheral edge and a surface extending thereabout and a longitudinal axis formed through an apex of said shield member, said shield member being formed at least in part of flexible and pliant material for selectively shaping said peripheral edge to fit the shape or dimension of a wound, and comprising an aperture formed through said shield member providing egress for fluid from therebeneath;
    a drain tube configured for attachment to said aperture; and
    an adjustable hub extending from said surface of said shield member, said hub being configured to be circumferentially adjustable in shape or dimension at a flexible, circumferentially elastic, throat to adapt to a plurality of sizes in the fluid end portion of fluid delivery devices, whereby to maintain engagement between said splash shield and one of said fluid delivery devices.

2. The splash shield of claim 1 wherein said shield member is constructed in an area about the positioning of said hub through said shield member to impart angular movement to said hub relative to said shield member to selectively modify the angle at which irrigating liquid is directed to a wound.

3. The splash shield of claim 2 wherein said surface of said shield bears indicia in proximity to said hub to indicate the degree of modification of the angularity of said hub relative to said longitudinal axis of the shield member.

4. The splash shield of claim 1 wherein said hub is positioned away from said apex of said shield member and oriented to direct irrigating liquid to a wound at an angle to said longitudinal axis.

5. The splash shield of claim 1 wherein said flexible throat is longitudinally elastic.

6. The splash shield of claim 1 wherein said adjustable hub comprises a flexible collar at least a portion of which is circumferentially elastic.

7. The splash shield of claim 6 wherein said flexible collar further comprises an outer portion and an inner portion connected thereto, said inner portion being circumferentially elastic.

8. The splash shield of claim 1 wherein said peripheral edge is linear.

9. A splash shield for use in wound irrigation comprising:
    three-dimensional shield member having a peripheral edge and a surface extending thereabout and a longitudinal axis formed through an apex of said shield member, said shield member being formed at least in part of flexible and pliant material enabling manipulation of said peripheral edge in a radial direction toward and in proximity to said longitudinal axis to provide shaping of said peripheral edge to fit the shape or dimension of a wound; and
    a hub connected to said shield member, said hub comprising a flexible, circumferentially elastic, throat configured to receive a plurality of different fluid delivery devices having different shapes for delivering irrigating fluid within said shield member and to a wound site, said throat having sufficient flexibility for an outer lip thereof to be everted and subsequently rolled back up to extend a portion of said throat over an inserted fluid end portion of a fluid delivery device, whereby to establish a self-biased engagement between said throat and said end portion.

10. A splash shield for use in wound irrigation comprising:
    a three-dimensional shield member having an open end circumscribed by a peripheral edge with a surface extending thereabout substantially to define a volume with a longitudinal axis being formed through an apex of said shield member, said shield member being formed at least in part of flexible and pliant material enabling manipulation of said peripheral edge in a radial direction toward or away from said longitudinal axis to provide shaping of said peripheral edge; and
    a hub connected to said shield member, said hub being configured to receive fluid dispensing end portions of a plurality of different fluid delivery devices and end portions comprising different sizes, and for delivering therethrough irrigating fluid into said volume and to a wound site while resisting contact between a said end portion and a wound being irrigated, said hub comprising an eccentric rotatable cuff operable to reduce the size of an opening through said hub thereby to secure said splash shield to a said dispensing end portion; wherein;
    material comprising said shield member in a region adjacent said hub and said hub is structured in a combination for flexing to permit the angle of delivered irrigation fluid to be selectively modified.

11. The splash shield according to claim 10, said hub comprising a flexible, circumferentially elastic, throat extending outwardly from said surface of said shield member, with a portion of said throat being expandable in shape to engage a fluid dispensing end portion of one of said fluid delivery devices.

12. The splash shield according to claim 10, said hub comprising a flexible, circumferentially elastic, tubular throat between a first open end having a first diameter through which to receive a said dispensing end portion, and a second open end having a second diameter, wherein said first diameter is larger than said second diameter.

13. The splash shield according to claim 10, further comprising a drain tube connected to said shield member and extending away from said shield member.

14. A splash shield for use in wound irrigation comprising:

a three-dimensional shield member having a peripheral edge and a surface extending thereabout and a longitudinal axis formed through an apex of said shield member, said shield member being formed at least in part of flexible and pliant material for selectively shaping said peripheral edge to fit the shape or dimension of a wound;

a drain tube connected to said shield member near said peripheral edge and extending away from said shield member; and an adjustable hub extending from said surface of said shield member, said hub being configured to be circumferentially adjustable in shape to dimension at a flexible, circumferentially elastic, throat to adapt to a plurality of sizes in the fluid end portion of fluid delivery devices, whereby to maintain engagement between said splash shield and one of said fluid delivery devices.

15. A splash shield for use in wound irrigation comprising:

a three-dimensional shield member having a peripheral edge and a surface extending thereabout and a longitudinal axis formed through an apex of said shield member, said shield member being formed at least in part of flexible and pliant material for selectively shaping said peripheral edge to fit the shape or dimension of a wound, said shield member being partially rigid in construction with rigid longitudinal ribs extending from the apex of said shield member to said peripheral edge; and an adjustable hub extending from said surface of said shield member, said hub being configured to be circumferentially adjustable in shape or dimension at a flexible, circumferentially elastic, throat to adapt to a plurality of sizes in the fluid end portion of fluid delivery devices, whereby to maintain engagement between said splash shield and one of said fluid delivery devices.

* * * * *

UNITED STATES PATENT AND TRADEMARK OFFICE
CERTIFICATE OF CORRECTION

PATENT NO.     : 6,402,724 B1                                                Page 1 of 1
DATED          : June 11, 2002
INVENTOR(S)    : Steven M. Smith, Mark A. Christensen and Deborah K. Jacobson It is certified that error appears in the above-identified patent and that said Letters Patent is hereby corrected as shown below:

Column 4,
Line 29, after "Pik" and before "TM" delete "-"

Column 10,
Line 21, before "three-dimensional" insert -- a --

Column 12,
Line 1, after "shape" change "to" to -- or --

Signed and Sealed this

Eighth Day of April, 2003

JAMES E. ROGAN
*Director of the United States Patent and Trademark Office*